United States Patent [19]

Hutchings et al.

[11] Patent Number: 5,726,326
[45] Date of Patent: Mar. 10, 1998

[54] THIOPHENE SYNTHESIS

[75] Inventors: Graham John Hutchings, Osmotherley; Richard William Joyner, Liverpool; Barry William Luke Southward, Widnes; Russel Andrew Stewart, Wolverhampton; Lance Svend Fuller, Acton Trussell, all of England

[73] Assignee: Shell Research Limited, Waterloo, England

[21] Appl. No.: 669,015

[22] Filed: Jun. 24, 1996

[30] Foreign Application Priority Data

Jun. 28, 1995 [EP] European Pat. Off. ............ 95304562

[51] Int. Cl.$^6$ ...................... C07D 333/08; C07D 333/10
[52] U.S. Cl. .................... 549/85; 549/84; 549/83
[58] Field of Search .................. 549/85, 84, 83, 549/29

[56] References Cited

U.S. PATENT DOCUMENTS

| 2,694,074 | 11/1954 | Kemp, Jr. | 549/85 |
| 3,822,289 | 7/1974 | Clark et al. | 549/85 |
| 3,939,179 | 2/1976 | Bell et al. | 549/85 |

Primary Examiner—Deborah Lambkin

[57] ABSTRACT

A method of preparing a thiophene comprises reacting an organic compound containing a chain of at least 4 C atoms linked by single or double bonds with a source of sulphur in the vapor phase, in the presence of a supported catalyst, the catalyst having the composition $$(Fe_{0.1}M_{1-0})O_n$$

wherein M is a metal of Group VA, VIA or VIIA; and n is an appropriate value.

14 Claims, No Drawings

THIOPHENE SYNTHESIS

This invention relates to a method for preparing thiophenes. Various syntheses of thiophene and its homologues are known. For example, GB-A-1345203 describes the reaction of an organic compound containing a consecutive chain of at least 4 carbon atoms linked by single or double bonds, and optionally carrying substituents, with carbon disulphide, in the vapour phase, and in the presence of a catalyst. The catalyst may be an oxidation, dehydrogenation or dehydration catalyst, e.g. chromia-alumina, molybdenum oxide or manganese oxide, and is preferably promoted by alkali or alkaline earth metal.

Stobbe et al, J. Catalysis 134:533–547 (1992), describe iron oxide dehydrogenation catalysts supported by magnesium oxide and promoted by potassium. It is suggested that $KFeO_2$ is formed, and that this retards the reduction of iron oxide to metallic iron.

The present invention is based on the discovery that supported iron oxide catalysts are useful in the synthesis of thiophenes, and that the catalytic effect can be enhanced by part or whole substitution of the Fe content by other Group VA, VIA or VIIA metals (M) such as V, Mn and Cr (III). Accordingly, the invention comprises a method of preparing a thiophene by reacting an organic compound containing a chain of at least 4 C atoms linked by single or double bonds with a source of sulphur in the vapour phase, in the presence of a supported catalyst, the catalyst having the composition $$(Fe_{0.1}M_{1-0})O_n$$

wherein M is a metal of Group VA, VIA or VIIA; and n is an appropriate value. Preferably, Fe and M are both present. In this case, while the range of Cr or other M substitution may be up to 20%, it is preferably 1–15%, more preferably 2–10% and most preferably 2–7%, e.g. about 5%.

It is preferred to use a promoter. For example, it is often desirable to include in the catalyst some alkali or alkaline earth metal, which is generally added to the catalyst after the formation of the catalyst has otherwise been completed. Preferred alkali metals are potassium and sodium. Examples of alkaline earth metals are calcium and barium.

The addition of potassium or other alkali or alkaline earth metal can be made to a preformed catalyst by adding potassium carbonate or some other alkali compound. The amount of alkali or alkaline earth metal compound present on the catalyst can be, for example, from 4–20% by weight, calculated as potassium carbonate.

Supports that are conventional in the catalyst field may be used, but the preferred catalyst support is MgO. γ-Alumina, and silica are also suitable.

The catalyst itself is known or may be prepared by known procedures. A suitable procedure is given in the Examples, below.

The starting materials that may be used in the method of the invention are organic compounds containing a consecutive chain of at least 4 carbon atoms linked by single or double bonds. Any of the carbon atoms of the chain may be unsubstituted or they may be individually substituted by a group such as hydroxyl, oxygen, alkyl, aralkyl or aryl. Optionally, two adjacent carbon atoms in the chain may form part of an aromatic or heterocyclic ring system. Examples therefore include alkanes, olefins, ketones, aldehydes and alcohols, and the alkanes may be substituted by, for example, aryl.

The choice of starting material controls the thiophene that is obtained. Thus, a starting material containing solely 4 carbon atoms in a straight chain will produce thiophene while a starting material containing more than 4 carbon atoms will produce a substituted thiophene.

The starting compound may be an alcohol, and the alcohol can be a dihydric alcohol or it can be unsaturated. It may be substituted by one or more substituents individually selected from hydrogen, alkyl, aryl, aralkyl or heterocyclic substituents. A suitable heterocyclic substituent is pyridyl. A typical unsubstituted starting alcohol is but-2-enol and a typical dihydric alcohol is 1,4-butanediol.

By way of example, if the starting material is n-butanol, the product is thiophene. Further, a pentanol will yield a methylthiophene, 1-hexanol yields 2-ethyl-thiophene and 1-heptanol yields 2-propylthiophene. If that starting alcohol is substituted at the 2- and/or 3-positions, the thiophene will be substituted in the 3- and/or 4-positions. For example, 2-ethylbutan-1-ol yields 3-ethylthiophene.

Other starting materials that may be used include olefins. They may have more than one unsaturated position and may be substituted as indicated for alcohols. Suitable olefins include butadiene, isoprene and butenes such as 2-methylbut-1-ene.

A variety of ketones or aldehydes can be used as starting material. Broadly any ketone or aldehyde having a carbon skeleton substituted as defined above for alcohols could be used. Examples are butyraldehyde, crotonaldehyde, butenal and methyl isobutyl ketone. Similarly, a wide variety of alkanes can be used, and again any alkane having a carbon skeleton of 4 consecutive carbon atoms, but which can also be substituted, can be used.

Particularly useful starting materials include those comprising a benzene ring substituted by a straight chain of 2 or more carbon atoms since these can result in the formation of benzothiophenes. For example, reaction of ethyl benzene in the process of the invention results in the formation of benzo(b) thiophene; sec-butylbenzene will give 3-phenylthiophene.

A range of sulphur-containing feedstock materials can be used. Examples include carbon disulphide, hydrogen sulphide, carbonyl sulphide and sulphur. Carbon disulphide is preferred.

The temperature of the reaction is suitably between 300° and 650° C., preferably between 375° C. and 500° C., since at lower temperatures conversion of the starting compound and yield of desired thiophene drops sharply, and there is no particular merit in operating at higher temperatures. The fact that good conversion can be achieved at up to 500° C. is an important advantage of this invention.

Provided there is sufficient carbon disulphide present it is easily possible to achieve substantially complete conversion of the starting compound, for example 95% or more, often 99% or more. This is especially desirable when the starting material is an alcohol, since thiophene and its homologues tend to form azeotropes with the alcohols that may be used, with the result that separation of the thiophene from admixture with the alcohol could be difficult.

The mole ratio of carbon disulphide to the starting material may be from 4:1 to 0.1:1, preferably from 2:1 to 1:1. Thus, an excess over the equimolar amount of carbon disulphide can be used.

The contact time with the catalyst is usually between 0.1 and 20 seconds. Preferably, it is 4 to 8 seconds, with the best results often being achieved at about 5 seconds. Higher values tend to reduce the yield of thiophene, while maintaining high conversion, while lower values tend to reduce both the conversion and the amount of product obtained.

The reaction is normally conducted at atmospheric pressure but higher or lower pressures may be used.

It is known that catalysts for this reaction lose activity, due to the accumulation of coke. In the event of this occurring, the catalysts may be regenerated by heating in air, or with steam/air mixtures.

The following Examples illustrate the invention.

EXAMPLE 1

The desired wt % of Cr III and Fe III sulphates (5% Cr: 95% Fe) were dissolved in hot distilled water, to which the desired wt % of $K_2CO_3$ and MgO (prepared from a two-step calcination of the hydroxide) were added. The resulting mixture was evaporated to a paste, dried in air for 24 hours and then in an oven at 120° C. for a further 24 hours, prior to calcination at 700° C. for 24 hours. The resulting material was meshed to 0.6–1.0 mm and stored in a desiccator (to avoid unwanted adsorption of water from the atmosphere).

Using this catalyst, which may be represented as $K_2Mg(Fe_{0.95}Cr_{0.05})3$, 3-methylthiophene was produced by the reaction of equimolar amounts of 2-methylbutanol and carbon disulphide with an approximate LHSV of 1 hr, over a range of temperatures, in a microreactor under a flow of nitrogen.

The yield of 3-methylthiophene (3 MT) was 97.6% at a conversion of 100% in a run conducted under these conditions and at a temperature of 475° C.

EXAMPLE 2

Using a comparable catalyst system, supported on CaO, gave yields of 3 MT up to 67%, at a conversion of 80%.

EXAMPLE 3

The catalyst of this example was prepared comparably with that in example 1, but using potassium nitrate or carbonate as the source of the promoter metal. The results of tests in producing 3 MT from 2- methylbutanol at 475° C. using these catalysts showed 88.2% yield of 3 MT at 90% conversion.

EXAMPLE 4 and 5

Catalysts on a magnesia, MgO, support were prepared comparably to example 1, but with the omission of iron from the catalyst composition, i.e. all the M(III) metal ion was chromium metal. In example 4 there was no alkali metal promotion of the catalyst and only moderate yields of 3 MT were obtained, but with significant levels of conversion of the feedstock 2-methylbutanol. In example 5, the catalyst was promoted with potassium and the performance of the catalyst is similar to that of example 1 at 475° C., a yield of 3 MT at 95.4% at a conversion of 97.6% being obtained.

EXAMPLE 6

The effect of different metal (M) components was studied using vanadium M(III) ion in combination with iron (Fe). The catalyst was prepared comparably to that in example 1, but with the chromium sulphate being replaced by the vanadium sulphate. 2-Methylbutanol was the feedstock material and reactions were carried out at 400° C. and at 475° C.

The results show that a molar yield of 3 MT of 90.0% at 400° C. and 96.9% at 475° C. 100° conversion occurs at 400° C. with the vanadium catalyst, which is not observed with the chromium catalyst, example 1, until 425° C.

EXAMPLE 7

A catalyst incorporating the active metal oxide system was prepared comparably to that in example 1, but with the active metal oxide system supported on gamma alumina instead of magnesia. Reactions using 2-methylbutanol with these catalysts produced 89.8% 3 MT with 97.3% conversion at 400° C., and 95.6% 3 MT with 100% conversion at 475° C.

What is claimed is:

1. A method of preparing a thiophene, which comprises reacting an organic compound containing a chain of at least 4 C atoms linked by single or double bonds with a source of sulphur in the vapour phase, wherein said sulphur source is carbon disulphide, in the presence of a catalyst supported with magnesia, alumina or silica, the catalyst having the composition

wherein M is a metal of Group VA, VIA or VIIA; and n is an appropriate value.

2. A method according to claim 1, wherein Fe and M are both present and M is V, Mn or Cr.

3. A method according to claim 2, wherein the Fe:M ratio is

4. A method according to claim 1, wherein the catalyst is promoted by a source of potassium.

5. A method according to claim 2, wherein the catalyst is promoted by a source of potassium.

6. A method according to claim 3, wherein the catalyst is promoted by a source of potassium.

7. A method according to claim 4, wherein the potassium source is potassium carbonate.

8. A method according to claim 5, wherein the potassium source is potassium carbonate.

9. A method according to claim 6, wherein the potassium source is potassium carbonate.

10. A method according to claim 1, in which the reaction is conducted at 300° to 650° C.

11. A method according to claim 2, in which the reaction is conducted at 300° to 650° C.

12. A method according to claim 3, in which the reaction is conducted at 300° to 650° C.

13. A method according to claim 4, in which the reaction is conducted at 300° to 650° C.

14. A method according to claim 7, in which the reaction is conducted at 300° to 650° C.

* * * * *